(12) United States Patent
Lancieux et al.

(10) Patent No.: US 8,794,963 B2
(45) Date of Patent: Aug. 5, 2014

(54) DEVICE FOR CENTERING AND GUIDING A DRILL BIT OF A DENTAL HANDPIECE

(75) Inventors: Cédric Lancieux, Passy (FR); Hervé Richard, Notre Dame de Bellecombe (FR)

(73) Assignee: Anthogyr, Sallanches (FR)

(*) Notice: Subject to any disclaimer, the term of this patent is extended or adjusted under 35 U.S.C. 154(b) by 324 days.

(21) Appl. No.: 12/808,870

(22) PCT Filed: Dec. 19, 2008

(86) PCT No.: PCT/IB2008/055471
§ 371 (c)(1),
(2), (4) Date: Jun. 17, 2010

(87) PCT Pub. No.: WO2009/081375
PCT Pub. Date: Jul. 2, 2009

(65) Prior Publication Data
US 2010/0311006 A1    Dec. 9, 2010

(30) Foreign Application Priority Data
Dec. 20, 2007  (FR) ...................... 07 60175

(51) Int. Cl.
*A61C 3/00*   (2006.01)
*A61C 1/08*   (2006.01)
*A61C 8/00*   (2006.01)
*A61B 19/00*  (2006.01)

(52) U.S. Cl.
CPC ........... *A61C 1/084* (2013.01); *A61B 2019/306* (2013.01); *A61C 8/0089* (2013.01)
USPC .............................................. 433/75; 606/96

(58) Field of Classification Search
USPC ............................. 433/72, 75–76; 606/96–98
See application file for complete search history.

(56) References Cited

U.S. PATENT DOCUMENTS

| | | | | | |
|---|---|---|---|---|---|
| 1,831,813 | A | * | 11/1931 | Levedahl | 408/81 |
| 2,338,765 | A | * | 1/1944 | Hartman | 408/81 |
| 3,540,322 | A | * | 11/1970 | Swanson | 408/112 |
| 3,838,517 | A | * | 10/1974 | Michnick | 433/72 |
| 4,138,200 | A | * | 2/1979 | Nazarenus | 408/241 S |
| 4,998,881 | A | * | 3/1991 | Lauks | 433/173 |
| 6,514,258 | B1 | * | 2/2003 | Brown et al. | 606/80 |

(Continued)

FOREIGN PATENT DOCUMENTS

| | | |
|---|---|---|
| EP | 1733695 A1 | 12/2006 |
| EP | 1759658 A1 | 3/2007 |

(Continued)

*Primary Examiner* — Hao D Mai
(74) *Attorney, Agent, or Firm* — William H. Eilberg

(57) ABSTRACT

A device for centering and guiding at least one drill bit of a dental handpiece when drilling a hole in the jaw of a patient in cooperation with a surgical guide equipped with a tubular drill bushing. A support holds a tubular guide sleeve permanently in a coaxial and sliding position with respect to the drill bit. The tubular guide sleeve is able to engage with slight play in the tubular drill bushing. The support insures the engagement of the guide sleeve in the tubular drill bushing at the latest when the drill bit starts to drill in the patient's jaw, thus insuring the centering and guiding of the drill bit.

18 Claims, 7 Drawing Sheets

(56) References Cited

U.S. PATENT DOCUMENTS

| | | | |
|---|---|---|---|
| 6,537,067 B1 * | 3/2003 | Wennemann | 433/76 |
| 6,739,872 B1 | 5/2004 | Turri | |
| 7,141,074 B2 * | 11/2006 | Fanger et al. | 606/80 |
| 2005/0170311 A1 | 8/2005 | Tardieu | |
| 2010/0047737 A1 | 2/2010 | Richard | |
| 2010/0129768 A1 * | 5/2010 | Isidori | 433/75 |

FOREIGN PATENT DOCUMENTS

| | | |
|---|---|---|
| FR | 2880534 A1 | 7/2006 |
| FR | 2882250 A1 | 8/2006 |
| WO | 0074585 A2 | 12/2000 |
| WO | 03071972 A1 | 9/2003 |
| WO | 2004098435 A2 | 11/2004 |

\* cited by examiner

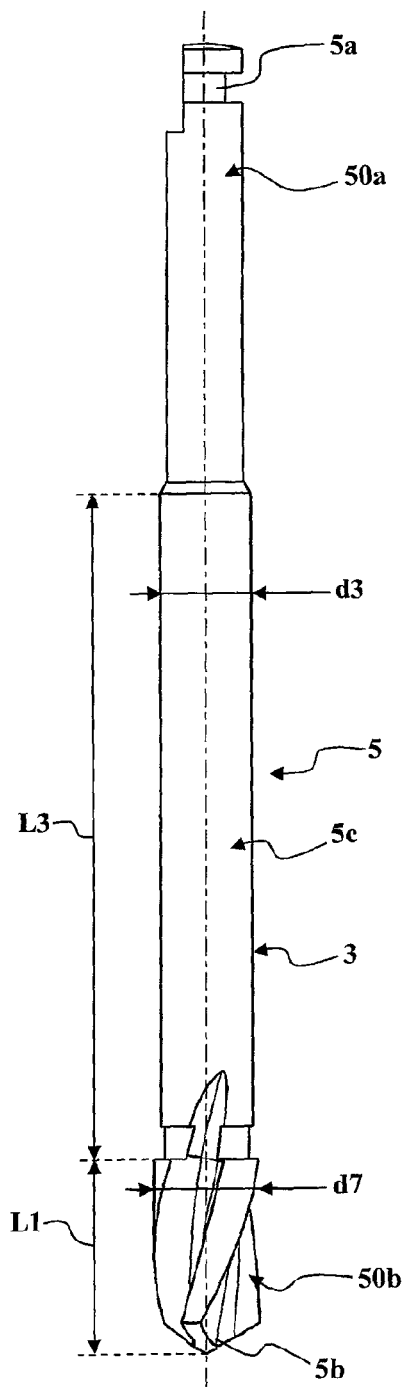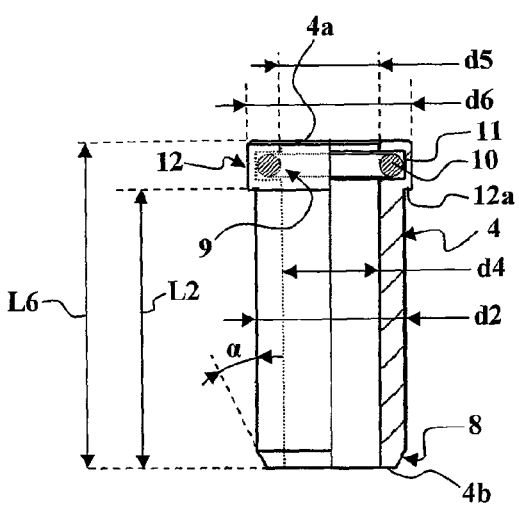
FIG. 1
FIG. 2

DEVICE FOR CENTERING AND GUIDING A DRILL BIT OF A DENTAL HANDPIECE

TECHNICAL FIELD OF THE INVENTION

The present invention concerns dental implants and more particularly installing dental implants assisted by a surgical guide placed in the mouth of the patient.

To replace damaged teeth in the mouth of a patient, implants fixed into the jawbone of the patient have been used for many years. After drilling a hole in the jawbone of the patient using a dental handpiece, the proximal part of an implant is screwed into the hole after which its distal part receives a dental prosthesis.

To assist the practitioner to produce the holes in the jawbone of the patient, surgical guides have been used for a number of years that the practitioner can fit in the patient's mouth on their jaw. This kind of surgical guide is an arcuate structure that follows the curvature of the jaw and that is provided with one or more tubular drilling bushes that extend as far as the vicinity of the area of the jawbone to be drilled. These surgical guides are produced using three-dimensional X-rays of the patient's jaw, enabling the tubular drilling bushes to be positioned very accurately.

These tubular drilling bushes have an interior bore of constant and standardized diameter. At present, the most widely used diameters are 4.2 mm and 5.2 mm, for example.

The problem arises that, when drilling the jawbone of the patient to fit an implant, the practitioner uses in succession a plurality of drill bits of different diameters driven in rotation by the dental handpiece to make firstly a hole of small diameter that is then enlarged up to the nominal diameter of the implant to be fitted, which generally corresponds to the diameter of the interior bore of the tubular drilling bush, namely 4.2 mm or 5.2 mm, for example, for those most widely used.

Drilling in a number of passes using drill bits of increasing diameter limits the heating of the jawbone to prevent necrosis.

To drill a hole accurately in the patient's jawbone, great geometrical accuracy is necessary and in particular it is necessary to guarantee that the successive drill bits are perfectly coaxial with the tubular drilling bush.

To enable good geometrical accuracy and the use of a plurality of drill bits of different outside diameters, it has been proposed to use a plurality of tubular guide sleeves each adapted to be engaged with a small clearance in the tubular drilling bush and each having an internal bore of constant diameter substantially equal to the outside diameter of the drill bit to be used. Thus for each drill bit having a particular diameter there corresponds a tubular guide sleeve adapted to cooperate with the tubular drilling bush of the surgical guide.

Such a solution has the drawback of increasing the number of parts necessary and obliges dental equipment manufacturers to use color codes to assist the practitioner to distinguish between the different sizes of tubular guide sleeve. However, there remains a risk of a practitioner using a tubular guide sleeve with an internal bore of greater diameter than the outside diameter of the drill bit, which may lead to drilling a hole that is not coaxial with the tubular drilling bush of the surgical guide.

To this problem of making sure that drill bits with different outside diameters remain coaxial is added the problem of drilling holes of chosen and progressively increasing depth when producing the hole for the implant, again with the aim of avoiding necrosis.

To this end, each tubular guide sleeve with an internal bore of a particular diameter adapted to a drill bit is replaced by a plurality of tubular guide sleeves with the same inside diameter but different heights, adapted to serve as positive end stops at the end of penetration of the drill bit into the jawbone of the patient when it reaches a required depth.

The practitioner therefore has to use too many parts during an operation, which dramatically increases the risk of error and the risk of contamination.

The document EP 1 759 658 proposes using a plurality of drill bits having different lengths with a shoulder fixed to the drill bits. If a practitioner attempts to drill the jaw in n passes of progressively increasing depth and p passes of progressively increasing diameters, the number of drill bits theoretically necessary is n×p, which means too many drill bits, too high a cost and too high a risk of errors and contamination.

The document EP 1 733 695 aims to guarantee a gap between two implants in the jaw of a patient. No drilling surgical guide is described: it is therefore not a matter, in the above document, of guaranteeing that a drill bit remains perfectly coaxial with a tubular drilling bush of a surgical guide.

STATEMENT OF THE INVENTION

A first problem addressed by the invention is to design a device for centering and longitudinally guiding at least one drill bit of a dental handpiece when drilling a hole in the jaw of a patient in cooperation with a surgical guide fitted with a tubular drilling bush that is simple and reliable in design, free of the risk of errors by the practitioner and ensures reliable centering and guiding of the drill bit.

At the same time, the present invention aims to provide a centering and longitudinal guiding device usable with a plurality of drill bits having different outside diameters.

The invention seeks further to minimize the number of parts to be used by the practitioner to drill holes for installing dental implants in the mouth of a patient at the same time as preserving high reliability of the geometrical positioning and depth of drilling.

To achieve the above and other objects, the invention proposes a device for centering and guiding at least one drill bit of a dental handpiece when drilling a hole for an implant in the jaw of a patient in cooperation with a surgical guide including a tubular drilling bush with an open upper end; according to the invention:
  a tubular guide sleeve is engaged with a small clearance in the tubular drilling bush,
  support means hold the tubular guide sleeve permanently coaxial with and slidable relative to said at least one drill bit, and
  the support means are adapted to cause engagement of the guide sleeve in the tubular drilling bush at the latest as soon as said at least one drill bit begins to drill the jaw of the patient.

Such a device is an effective answer to the problem stated above.

In a first embodiment of the invention, it may be provided that:
  said at least one drill bit may have a proximal end and a free distal end with a proximal section for connection to the dental handpiece and a distal cutting section, and
  the support means may include a smooth cylindrical intermediate section of said at least one drill bit with an outside diameter substantially equal to or slightly less than the inside diameter of the guide sleeve and on which the tubular guide sleeve is slidably engaged.

The centering and guiding device may preferably include a plurality of drill bits with distal cutting sections of different diameters and all having a smooth cylindrical intermediate section of the same outside diameter substantially equal to or slightly less than the inside diameter of the guide sleeve.

Such a centering and guiding device necessitates the use of only one tubular guide sleeve matched to the inside diameter of the drilling bush and usable with a drill bit or a plurality of drill bits with distal cutting sections with different outside diameters. The number of parts necessary for the practitioner to ensure guiding and good accuracy of drilling is thus extremely small.

Such a centering and guiding device is of very simple design, very simple for the practitioner to manipulate, greatly limits the risk of errors in the geometrical orientation of the drilling and has a very compact overall size so as not to impede the practitioner.

The guide sleeve may preferably include penetration means to facilitate its engagement in the tubular drilling bush, preferably in the form of a bevelled distal end.

The guide sleeve may advantageously include friction means adapted to slide on the smooth cylindrical intermediate section, preferably an O-ring having an inside diameter substantially equal to the outside diameter of the smooth cylindrical intermediate section and housed in an interior annular groove of the guide sleeve.

Such penetration means and/or such friction means facilitate penetration of the tubular guide sleeve into the tubular drilling bush without tending to ride up the drill bit too easily in the event of a lack of coaxiality between the guide sleeve and the tubular drilling bush when the practitioner begins to fit them one inside the other in order to cooperate.

The use of simple friction means, for example an O-ring, enables the practitioner to begin to slide the guide sleeve over the smooth cylindrical intermediate section of the drill bit by applying a first given force and then to continue this relative sliding between the guide sleeve and the drill bit by applying a second force substantially identical to the first force. There is therefore no jerk because of a sudden variation in the force produced by the friction means in reaction to the force applied by the practitioner, which could compromise drilling quality and accuracy.

Preferably, it may be provided that:
when in position on the jaw of the patient, the surgical guide may hold the open upper end of the tubular drilling bush at a particular first height above the distal end of the implant at the end of screwing it into the jaw of the patient, the first height preferably being approximately 9 mm,
the distal cutting section may have an axial length less than the first height, preferably between approximately 4 mm and approximately 7 mm, and
the distal cutting section may have an outside diameter greater than the outside diameter of the smooth intermediate section.

If the distal cutting section has an outside diameter greater than the outside diameter of the smooth intermediate section, the practitioner can easily position the guide sleeve in abutting engagement against the distal cutting section of the drill bit before drilling. The axial length of the distal cutting section relative to the first particular height is chosen to assure engagement of at least two to five millimeters of the tubular guide sleeve in the tubular drilling bush before the drill bit touches the jaw of the patient.

Advantageously, it may be provided that:
when in position on the jaw of the patient, the surgical guide may hold the open upper end of the tubular drilling bush at a particular first height above the distal end of the implant at the end of screwing it into the jaw of the patient, the first height preferably being approximately 9 mm,
the guide sleeve may have a proximal end with an outside diameter greater than the inside diameter of the tubular drilling bush and with a shoulder with an abutment face oriented in the direction of its distal end and intended to come to bear against the open upper end of the tubular drilling bush at the end of penetration of the guide sleeve into the tubular drilling bush,
the abutment face of the shoulder of the guide sleeve may be at a distance less than the first height from the distal end of the guide sleeve, advantageously between approximately 4 mm and approximately 8 mm inclusive, and preferably 8 mm.

Once the shoulder of the guide sleeve is abutted against the open upper end of the tubular drilling bush, the friction means rubbing on the smooth cylindrical intermediate section of the drill bit produce a reaction force that opposes the force that the practitioner applies to cause the drill bit to penetrate into the jawbone of the patient. A reaction force of this kind enables the practitioner to obtain a better idea of the stage the drilling has reached and to limit the speed of penetration into the jawbone, to avoid damaging it.

Finally, the abutment face of the shoulder of the guide sleeve being at a distance from the distal end of the guide sleeve less than the first height, it is impossible for the distal end of the guide sleeve to come into contact with the jaw of the patient, which guarantees good hygiene and prevents the guide sleeve damaging the operating area.

The device may advantageously further include adjustable means for limiting the depth of penetration of the drill bit in the jaw of the patient, preferably abutment means fastened to the dental handpiece and adapted to come to bear on the proximal end of the guide sleeve or on the open upper end of the tubular drilling bush at the end of penetration of the drill bit into the jaw of the patient.

Such adjustable means for limiting the depth of penetration of the drill bit can be of a known type, and the limiter and abutment devices generally supplied with dental handpieces may be used for this purpose. The practitioner can thus use a system familiar to them and well suited to their dental handpiece. A device of the type described in French patent application No. 06 54131 or French patent application FR 2 880 534 A1 may be used, for example.

The device may advantageously further include spring return means continuously urging the sliding guide sleeve toward the free distal end of the drill bit.

In a second embodiment of the invention, it may be provided that:
the guide sleeve may be movable on the support means between a low position and a high position,
the support means may be fastened to the dental handpiece and include adjustment means for adjusting the axial position of the guide sleeve relative to the drill bit when the guide sleeve is in the low position, and
in the high position, the first abutment means may prevent the guide sleeve from being moved further beyond the high position in the direction of the proximal end of the drill bit.

Such a solution enables use of a single guide sleeve fastened to the dental handpiece with a number of standard drill bits having different outside diameters less than the inside diameter of the guide sleeve.

Appropriate adjustment of the low position locates the distal end of the guide sleeve relative to the distal end of the drill bit to assure engagement of the latter in the drilling bush from the start of drilling.

Movement between the low position and the high position enables movement of the distal end of the drill bit relative to the guide sleeve to drill to the required depth.

The spring means carried by the support means may preferably continuously urge the guide sleeve in the direction of the free distal end of the drill bit toward the low position.

Such spring means make it possible to position the guide sleeve reliably from the beginning of drilling without intervention by the practitioner. This efficiently limits any risk of the drill bit coming into contact with the jawbone of the patient without being appropriately guided.

Such spring means also make it possible, during axial withdrawal of the drill bit from the jaw of the patient, to retain the guide sleeve in the tubular drilling bush during most of the withdrawal of the drill bit. This ensures that the drill bit is coaxial with the tubular drilling bush both when drilling and during most of the withdrawal of the drill bit from the jaw of the patient. Thus, this limits the risk of the drill bit damaging the walls of the hole it has produced when it is withdrawn.

Advantageously, it may be provided that:

the surgical guide may hold the open upper end of the tubular drilling bush at a particular first height above the distal end of the implant at the end of screwing it into the jaw of the patient, the first height preferably being approximately 9 mm, the guide sleeve may have an axial length less than the first height, advantageously between approximately 4 mm and approximately 8 mm, and the proximal end of the guide sleeve may be fastened to second abutment means adapted to come to bear against the open upper end of the tubular drilling bush at the end of penetration of the guide sleeve into the tubular drilling bush.

This avoids all risk of the distal end of the guide sleeve coming into contact with the jaw of the patient, which guarantees good hygiene and avoids all risk of causing lesions in the operating area.

Preferably, it may be provided that:

the second abutment means may include an abutment plate extending radially away from the longitudinal axis of the tubular guide sleeve, the first abutment means may include a support plate parallel to the abutment plate and situated in a plane offset longitudinally relative to the abutment plate, the support means may include two parallel guide columns providing a sliding connection between the support plate and the abutment plate, the spring means may include two coil springs interleaved between the abutment and support plates and urging the support plate and abutment plate away from each other, and the support means may include a longitudinal support rod fastened to the support plate and adapted to be fixed to the dental handpiece.

Advantageously, it may be provided that:

the longitudinal support rod may be formed with a rack, the dental handpiece may include a longitudinal sleeve for receiving the longitudinal support rod and locking means cooperating with the rack of the longitudinal support rod, the longitudinal receiving sleeve may include an internal bore with a cross section of complementary shape to the cross section of the longitudinal support rod, and the cross sections of the longitudinal support rod and the internal bore of the longitudinal receiving sleeve may prevent relative rotation between them.

In both of the first and second embodiments of the invention, the support means may be adapted to engage the guide sleeve in the tubular drilling bush to a distance substantially equal to the inside diameter of the tubular drilling bush, preferably greater than the inside diameter of the tubular drilling bush, and at the latest before said at least one drill bit begins to drill the jaw of the patient.

BRIEF DESCRIPTION OF THE DRAWINGS

Other objects, features and advantages of the present invention will emerge from the following description of particular embodiments of the invention, given with reference to the appended figures, in which:

FIG. 1 is a side view of a drill bit used in a first embodiment of the invention;

FIG. 2 is a part-sectional view of a guide sleeve used in the first embodiment of the invention;

DESCRIPTION OF PREFERRED EMBODIMENTS

Figure 3:
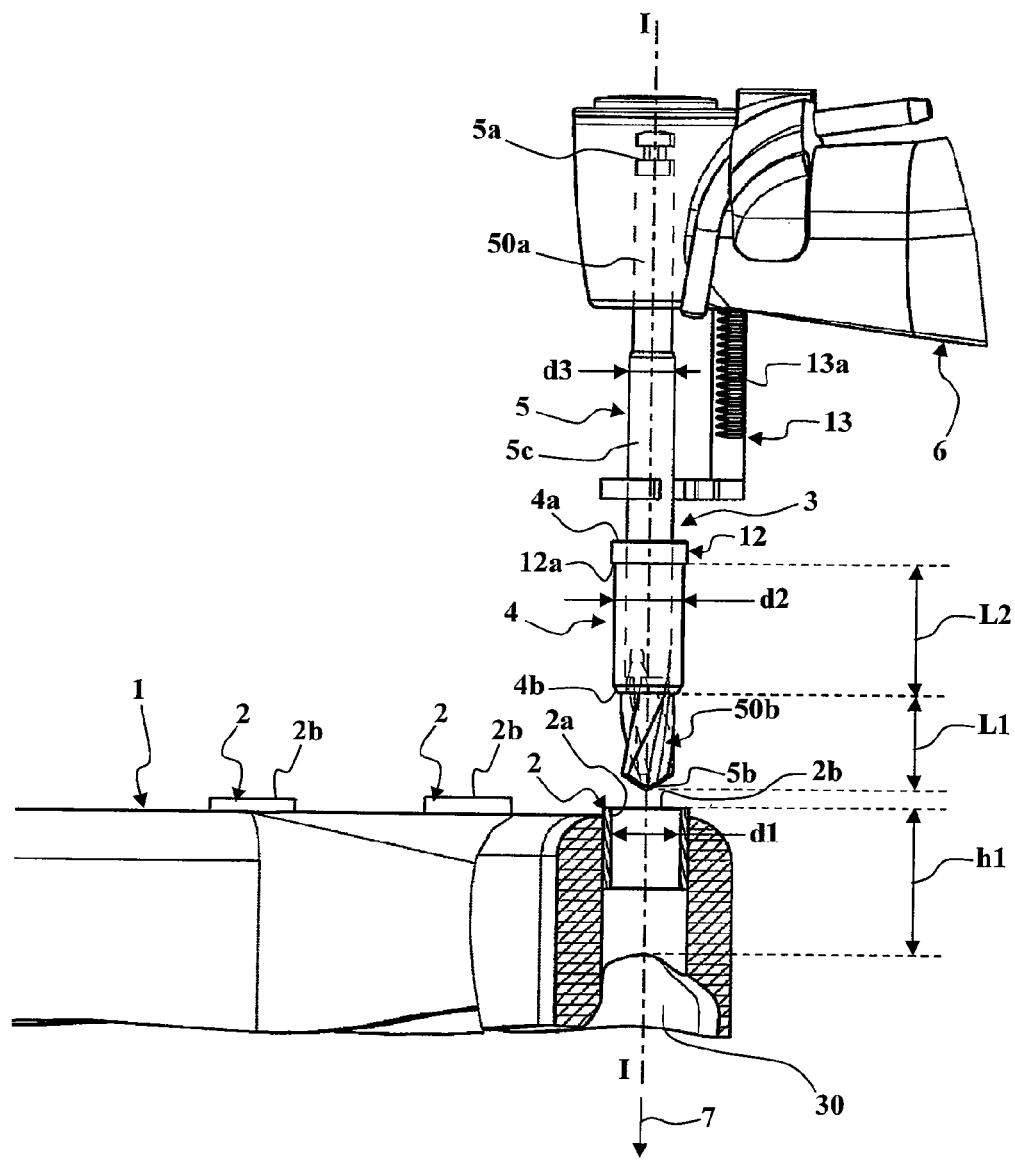
FIG. 3 is a side view showing the use of a centering and guiding device of the first embodiment of the invention.
Figure 8:
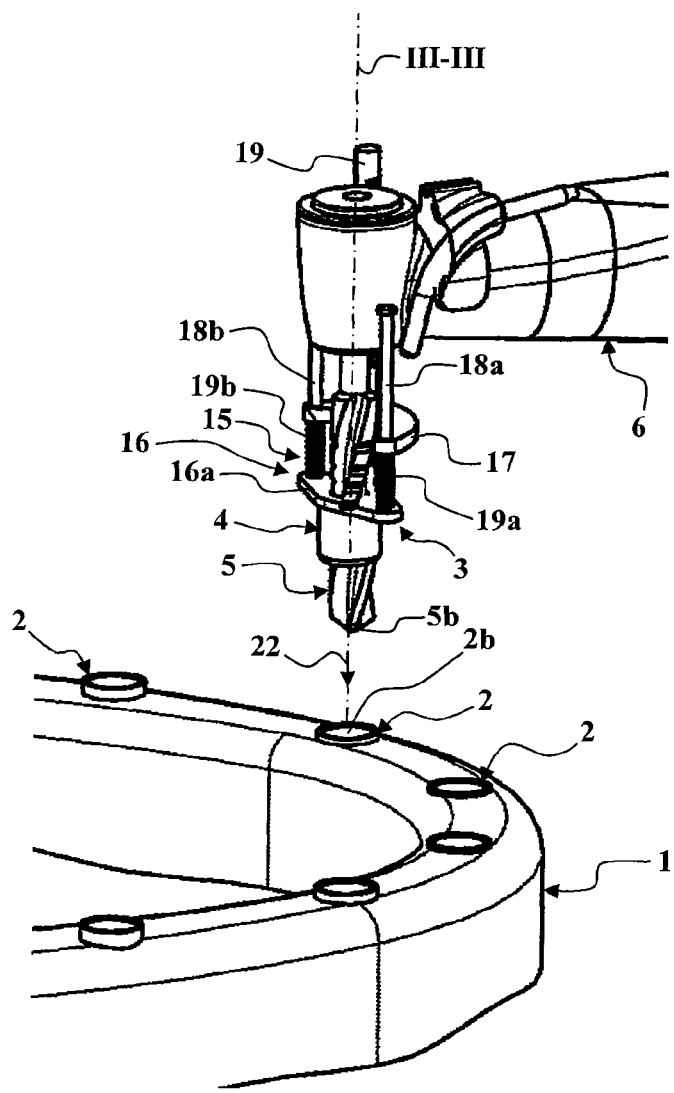
FIG. 8 is a perspective view showing the use of the device from FIGS. 5 and 6.

FIGS. 3 and 8 show a surgical guide 1 including a plurality of tubular drilling bushes 2 open at the upper end 2b. The surgical guide 1 enables a practitioner to drill a hole in the jaw 30 of a patient using a drill bit 5 carried by a dental handpiece 6. The tubular drilling bushes 2 make it possible to locate accurately the places where the holes must be produced to install the implants in the mouth of the patient. The tubular drilling bushes 2 have an internal bore 2a of diameter d1. The diameter d1 is standardized, and the most widely used values are 4.2 mm and 5.2 mm.

To produce the hole in the jaw of the patient accurately by ensuring that the hole is coaxial with the tubular drilling bush 2, the invention provides a drill bit centering and guiding device. Two different embodiments of such a device are shown in FIGS. 1 to 4, on the one hand, and FIGS. 5 to 9, on the other hand, respectively.

In these two embodiments of the invention, the centering and guiding device includes support means 3 that hold a tubular guide sleeve 4 permanently coaxial with and slidable relative to at least one drill bit 5.

The tubular guide sleeve 4 is adapted to fit with a small clearance in the tubular drilling bush 2 and to this end has an outside diameter d2 very slightly less than the diameter d1. By way of nonlimiting example, good results have been obtained using guide sleeves 4 with outside diameters d2 of 4.17 mm and 5.17 mm for tubular drilling bushes 2 with diameters d1 of 4.2 mm and 5.2 mm, respectively.

Once the tubular guide sleeve 4 is engaged in the tubular drilling bush 2, the latter assures perfect centering and longitudinal guiding of the drill bit 5 via the support means 3. During use of the centering and guiding device of the invention, the support means 3 make possible engagement of the guide sleeve 4 in the tubular drilling bush 2 at the latest as soon as the drill bit 5 begins to drill the jaw 30 of the patient.

In the first embodiment of the invention (FIGS. 1 to 4), the drill bit 5 has a proximal end 5a, a distal free end 5b, a proximal section 50a for connecting it to the dental handpiece 6 and a distal cutting section 50b.

The support means 3 include a smooth cylindrical intermediate section 5c of the drill bit 5 with an outside diameter d3 substantially equal to or slightly less than the inside diameter d4 of the guide sleeve 4 and on which the tubular guide sleeve 4 may be slidably engaged.

During use of the first embodiment of the invention (as shown in FIG. 3), the guide sleeve 4 is slidably disposed on the intermediate section 5c of the drill bit and makes it possible to guide the latter as it penetrates into the jaw 30 of the patient with a movement in the longitudinal direction I-I illustrated by the arrow 7.

The guide sleeve 4 is usable with a plurality of drill bits 5 with distal cutting sections 50b with different outside diameters d7 (FIG. 1), provided that they all include a smooth cylindrical intermediate section 5c of the same outside diameter d3 substantially equal to or slightly less than the inside diameter d4 of the guide sleeve 4.

This makes it possible for the practitioner, using one and the same guide sleeve 4, to use a plurality of drill bits 5 in succession to produce a hole in a plurality of passes with progressively increasing diameter and depth, thus avoiding necrosis of the jawbone of the patient in the vicinity of the hole.

It may be seen more particularly in FIG. 2 that the guide sleeve 4 includes penetration means 8 to facilitate its engagement in the tubular drilling bush 2. Here, the guide sleeve 4 is provided with a bevelled distal end 4b with a chamfer angle α of approximately 30°, for example.

To assure reliable positioning of the guide sleeve 4 on the intermediate section 5c of the drill bit 5 at the start of drilling, the guide sleeve 4 includes friction means 9 intended to rub on the smooth cylindrical intermediate section 5c. Here, the guide sleeve 4 includes an O-ring 10 with an inside diameter d5 slightly less than or substantially equal to the outside diameter d3 of the intermediate section 5c. The O-ring 10 is housed and held captive in an interior annular groove 11 of the guide sleeve 4.

The guide sleeve 4 also has a proximal end 4a with an outside diameter d6 greater than the inside diameter d1 of the tubular drilling bush 2 with a shoulder 12 with an abutment face 12a oriented in the direction of the distal end 4b. The shoulder 12 is intended to come to bear against the open top end 2b of the tubular drilling bush 2 at the end of penetration of the guide sleeve 4 into the tubular drilling bush 2.

Figure 10:
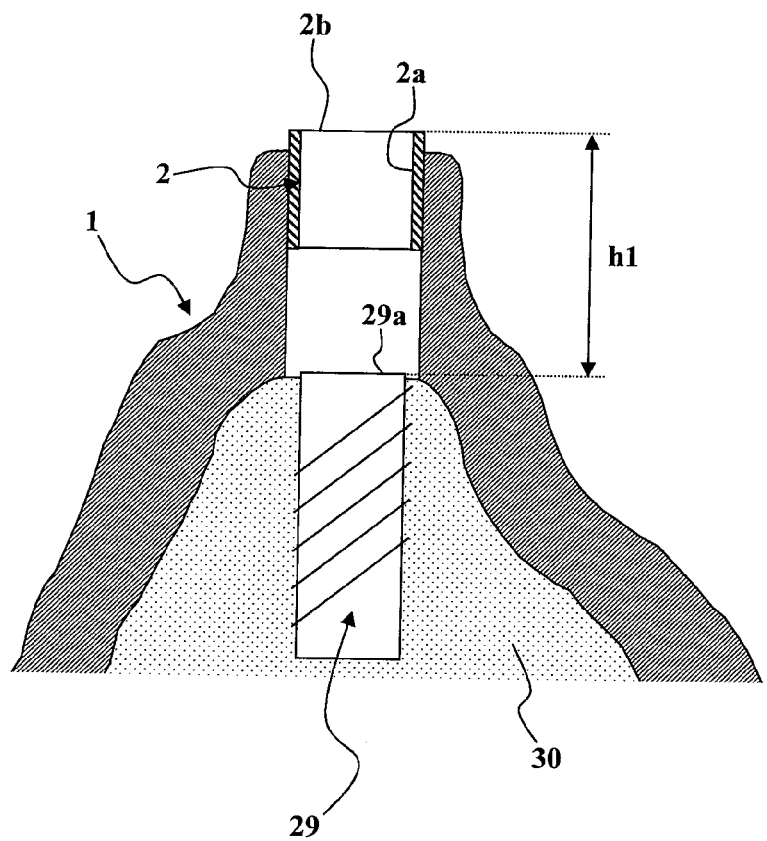
FIG. 10 is a diagrammatic part-sectional view of a surgical guide installed on the jaw of a patient.

It is seen more particularly in FIG. 10 that the surgical guide 1 holds the open upper end 2b of the tubular drilling bush 2 at a first particular height h1 on the distal end 29a of the implant 29 at the end of screwing it into the jaw 30 of the patient. In the standard manner well known to the person skilled in the art, the first height h1 is approximately 9 mm.

To assure accurate guiding of the drill bit 5 and good hygiene, the distal cutting section 50b has an axial length L1 (FIGS. 1 and 3) less than the first height h1 (FIG. 3) and preferably between approximately 4 mm and approximately 7 mm inclusive. The abutment face 12a of the shoulder 12 of the guide sleeve 4 is for its part at a distance from the distal end 4b of the sleeve 4 of L2 (FIGS. 2 and 3) that is also less than the first height h1 (FIG. 3) and advantageously between approximately 4 mm and approximately 8 mm. The distance L2 is preferably equal to approximately 8 mm when the first height h1 is 9 mm.

The distal cutting section 50b of the drill bit 5 advantageously has an outside diameter d7 greater than the outside diameter d3 of the smooth intermediate section 5c and the diameter of the proximal connecting section 50a which itself has a diameter less than or equal to the diameter d3 of the smooth intermediate section 5c, as shown in the figures. In practice, this enables the practitioner to thread the guide sleeve 4 over the drill bit 5 until the distal end 4b abuts against the distal cutting section 50b of the drill bit 5 before engaging the drill bit 5 in a tubular drilling bush 2, as shown more particularly in FIG. 3.

This disposition of the guide sleeve 4 and these distances L1 and L2 enable reliable guiding of the drill bit 5 even before it begins to drill the jaw of the patient, the guiding section being partially engaged in the tubular drilling bush 2 even before the drill bit 5 begins to drill the jaw of the patient.

The distance L2 being less than the first height h1, the guide sleeve 4 is not able to come into contact with the area of the jaw of the patient being operated on, which also guarantees good hygiene.

The guide sleeve 4 is fitted to the smooth intermediate section 5c of the drill bit 5 by threading it onto the drill bit 5 from its proximal end 5a. Thus the guide sleeve 4 does not rub on the distal cutting section 50b, which would risk damaging the guide sleeve 4 and/or the cutting edges of the drill bit 5. Where applicable, this also avoids the cutting edges of the drill bit 5 damaging the friction means 9, such as an O-ring 10, with the risk of producing particles of the O-ring that could pollute the drilled hole in the jaw and cause an infection or other unwanted reaction by the organism of the patient.

When using the guide sleeve 4, the friction means 9 are never in contact with the cutting edges of the drill bit 5, in order not to damage them.

To control the drilling depth of the drill bit 5, adjustable means are provided for limiting the depth of penetration of the drill bit 5 into the jaw 30 of the patient, as shown in FIG. 3. Here abutment means 13 are used that are attached to the dental handpiece 6 and intended to come to bear on the proximal end 4a of the guide sleeve 4 or on the open upper end 2b of the tubular drilling bush 2 at the end of penetration of the drill bit 5 into the jaw 30 of the patient.

To fit implants of the most widely used types, it is necessary to drill a hole with a depth between approximately 8 mm and approximately 15 mm. The intermediate section 5c therefore extends from the distal cutting section 50b over a first length L3 greater than the total length L6 of the guide sleeve 4 by at least approximately 8 mm, preferably at least approximately 15 mm.

In practice, when using the device of the first embodiment of the invention, the practitioner places a single guide sleeve 4 on the intermediate section 5c of a drill bit 5 to slide thereon. The guide sleeve 4 is disposed on the drill bit 5 with its distal end 4b abutted against the distal cutting section 50b.

The drill bit 5 is then mounted on the dental handpiece 6, which is provided with abutment means 13.

The abutment means 13 are adjustable in height, here by means of a rack 13a. Fixed-height abutment means may also be used, for example those described in French patent application FR 2 880 534 A1.

When the height of the abutment means 13 has been adjusted, the practitioner positions the drill bit 5 substantially coaxial with the tubular drilling bush 2 of the surgical guide 1 (FIG. 3). The practitioner then moves the drill bit 5 in the axial direction I-I illustrated by the arrow 7.

The distal cutting section 50b of the drill bit 5 enters the tubular drilling bush 2. The guide sleeve 4 is then engaged with small clearance in the tubular drilling bush 2 and centers and guides the drill bit 5 even before it touches the jaw 30 of the patient.

In the event of a slight defect of the coaxial positioning of the guide sleeve 4 relative to the tubular drilling bush 2 prior to engagement, the penetration means 8 and the friction means 9 facilitate engagement of the guide sleeve 4 in the tubular drilling bush 2 and prevent the latter from riding too easily up the drill bit 5.

Once it is coaxial with the tubular drilling bush 2, the guide sleeve 4 continues to penetrate into the tubular drilling bush 2 as the drill bit 5 advances into the jaw 30 of the patient. The distal end 4b of the guide sleeve 4 is still in the immediate vicinity or proximity of the distal cutting section 50b.

After a certain penetration of the drill bit 5 into the jaw 30 of the patient, the shoulder 12 of the guide sleeve 4 abuts against the open upper end 2b of the tubular drilling bush 2.

The guide sleeve 4 being slidably mounted on the intermediate section 5c of the drill bit 5, the drill bit 5 continues its axial movement illustrated by the arrow 7 until the abutment means 13 come to bear on the proximal end 4a of the guide sleeve 4 or on the open upper end 2b of the tubular drilling bush 2. The drill bit 5 cannot then continue its axial movement illustrated by the arrow 7 and the required drilling depth has been reached.

The practitioner can then withdraw the drill bit 5 axially with a movement opposite that illustrated by the arrow 7 in order to re-adjust the abutment means 13 to allow the drill bit 5 to drill deeper.

Once the satisfactory drilling depth has been reached (in one or more passes) with the aid of the drill bit 5, the practitioner can change the drill bit 5 and use another drill bit 5 with a distal cutting section 50b of greater outside diameter d7 in order progressively to enlarge the hole in the jaw of the patient.

To this end, the practitioner removes the guide sleeve 4 from the drill bit 5 of smaller diameter to fit it onto the intermediate section 5c of another drill bit 5 of greater diameter d7.

Example 1

Drilling a Hole in the Jaw of the Patient with a Device of the First Embodiment

In this example, the following choices are made:
h1 is made equal to 9 mm,
L1 is made equal to 5 mm,
L2 is made equal to 8 mm,
L3 is made equal to 30 mm,
L6 is made equal to approximately 10 mm,
d1 is made equal to 4.2 mm,
d2 is made equal to 4.17 mm,
d3 is made equal to 2.8 mm;
d4 is made equal to 2.8 mm (+clearance),
d5 is made equal to 2.8 mm (+clearance),
d6 is made equal to 4.6 mm.

The practitioner mounts the guide sleeve 4 on the intermediate section 5c with the distal end 4b abutted against the distal cutting section 50b and then fixes the drill bit 5 to the dental handpiece 6 fitted with abutment means 13. The practitioner then adjusts the height of the abutment means 13 to drill a hole of particular depth.

When the drill bit 5 comes into contact with the jawbone of the patient, the guide sleeve 4 is already engaged in the tubular drilling bush 2 to a distance of approximately 4 mm. This guides the drill bit 5 longitudinally even before the start of drilling, the guide sleeve 4 being engaged in the tubular drilling bush 2 to a distance more or less substantially equal to or greater than its outside diameter d2.

When the drill bit 5 has penetrated approximately 4 mm into the jawbone, the shoulder 12 abuts against the open upper end 2b: the guide sleeve 4 is immobilized relative to the tubular drilling bush 2 with its distal end 4b situated 1 mm above the operating area.

The practitioner then continues to drill the hole by sliding the intermediate section 5c of the drill bit 5 in the guide sleeve 4 until it reaches the final depth of the hole when the abutment means 13 abut against the proximal end 4a or against the open upper end 2b of the tubular drilling bush 2: the drill bit 5 can then not penetrate deeper into the jawbone.

Figure 4:
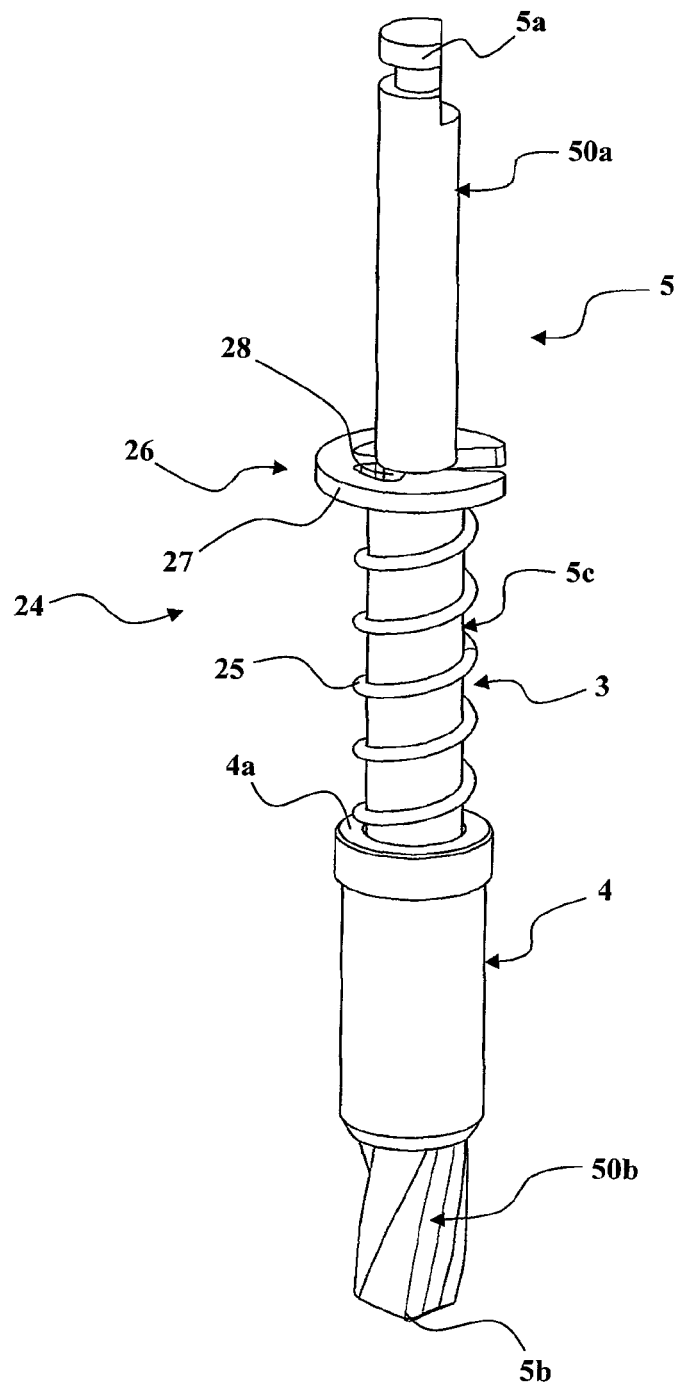
FIG. 4 is a perspective view of a variant of the first embodiment.

As well as or instead of the friction means 9, spring return means 24 may be provided, as shown in FIG. 4, to continuously urge the guide sleeve 4 to slide toward the free distal end 5b of the drill bit 5.

The spring return means 24 include a coil spring 25 engaged over the intermediate section 5c. The coil spring 25 bears against an upper abutment 26 and the proximal end 4a of the guide sleeve 4. The upper abutment 26 is simply provided by means of an outside circlip 27 engaged in an annular groove 28. Such an upper abutment 26 is easy and quick for the practitioner to fit and remove.

The spring return means 24 facilitate and render secure the engagement of the guide sleeve 4 in the tubular drilling bush 2 to guarantee that the drill bit 5 remains coaxial with the tubular drilling bush 2 when removing the drill bit 5 from the jaw, so as not to damage the walls of the hole it has produced.

Consider from now on FIGS. 5 to 9, which show a centering and guiding device of a second embodiment of the invention.

Figure 5:
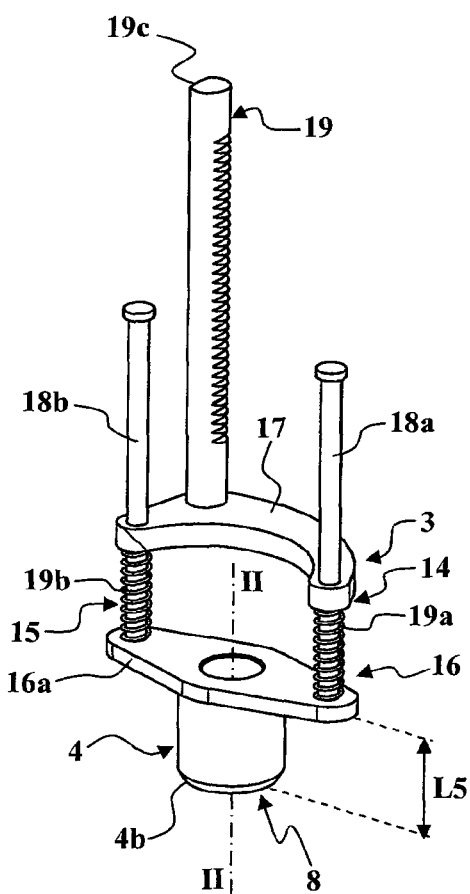
FIG. 5 is a perspective view of a centering and guiding device of a second embodiment of the invention with the guide sleeve in the low position.
Figure 6:
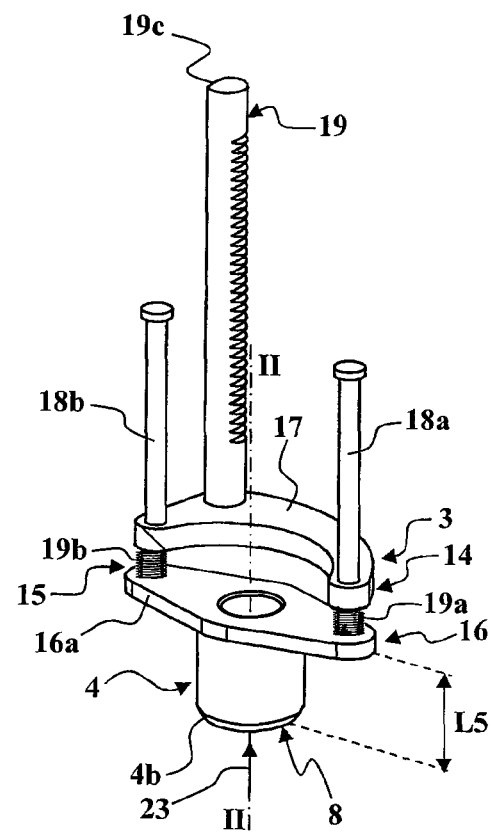
FIG. 6 is a perspective view of the device from FIG. 5 with the guide sleeve in the high position.

In this second embodiment, the guide sleeve 4 is movable relative to the support means 3 between a low position (FIG. 5) and a high position (FIG. 6).

The support means 3 are adjustable and fastened to the dental handpiece 6 (FIG. 8), and make it possible to adjust the axial position of the guide sleeve 4 relative to the drill bit 5 when the guide sleeve 4 is in the low position. In the high position, first abutment means 14 prevent the guide sleeve 4 moving further beyond the high position in the direction defined by the arrow 23 (FIG. 6).

It is seen more particularly in FIGS. 5 and 6 that the spring means 15 carried by the support means 3 allow axial movement of the guide sleeve 4 between its low position (FIG. 5) and its high position (FIG. 6). The spring means 15 continuously urge the guide sleeve 4 in the direction of the free distal end 5b of the drill bit 5, toward the low position.

Figure 7:
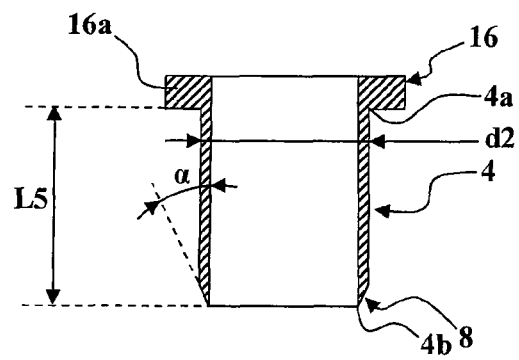
FIG. 7 is a view in longitudinal section of the guide sleeve of the second embodiment of the invention.

As represented in FIG. 7, the guide sleeve 4 includes penetration means 8 to facilitate its engagement in the tubular drilling bush 2. Here, the guide sleeve 4 has a bevelled distal end 4b with a chamfer angle α that may advantageously be made approximately 30°.

Exactly as in the first embodiment of the invention, the surgical guide 1 holds the open upper end 2b of the tubular drilling bush 2 at a first particular height h1 above the distal end 29a of the implant 29 at the end of screwing it into the jaw 30 of the patient, the first height h1 preferably being approximately 9 mm (FIG. 10). To prevent the guide sleeve 4 coming into conflict with the area of the jaw of the patient operated on and to guarantee improved hygiene, the guide sleeve 4 has an axial length L5 less than the first height h1 (FIG. 7). The axial length L5 is advantageously between approximately 4 mm and approximately 8 mm.

It is seen more particularly in FIG. 7 that the guide sleeve 4 is fastened at its proximal end 4*a* to second abutment means 16 adapted to come to bear against the open upper end 2*b* of the tubular drilling bush 2 at the end of penetration of the guide sleeve 4 into the tubular drilling bush 2. Here, the second abutment means 16 include an abutment plate 16*a* extending radially away from the longitudinal axis III-III of the tubular guide sleeve 4.

In FIGS. 5 and 6, the first abutment means 14 include a support plate 17 parallel to the abutment plate 16*a* and situated in a plane offset longitudinally relative to the abutment plate 16*a*.

The support means 3 include two parallel guiding columns 18*a* and 18*b* that provide a sliding connection between the support plate 17 and the abutment plate 16*a*.

The spring means 15 include two coil springs 19*a* and 19*b* interleaved between the abutment plate 16*a* and the support plate 17 and urging the support plate 17 and the abutment plate 16*a* away from each other. The support means 3 include a longitudinal support rod 19 fastened to the support plate 17 and adapted to be fixed to the dental handpiece 6.

Figure 9:
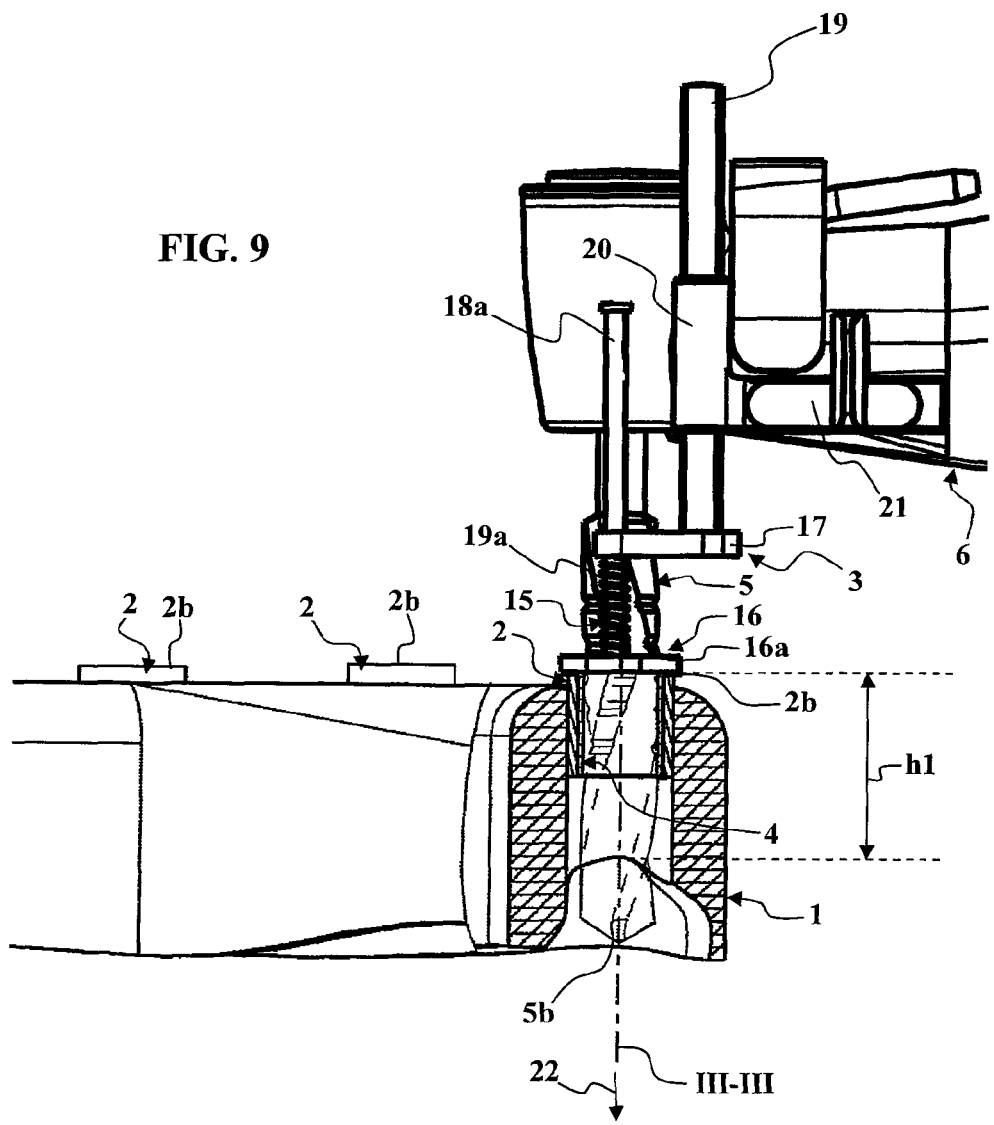
FIG. 9 is a side view showing the use of the device from FIGS. 5 and 6.

The longitudinal support rod 19 is formed with a rack and the dental handpiece 6 includes a longitudinal sleeve 20 for receiving the longitudinal support rod 19 (FIG. 9). The dental handpiece 6 further includes locking means 21 cooperating with the rack of the longitudinal support rod 19.

In order to receive the longitudinal support rod 19 with a small clearance, the longitudinal receiving sleeve includes an internal bore with a cross section of complementary shape to the cross section of the longitudinal support rod 19.

The cross sections of the longitudinal support rod 19 and the internal bore of the longitudinal receiving sleeve 20 prevent relative rotation between them.

Here, as seen in FIG. 5, the longitudinal support rod 19 has a flat 19*c* over its whole length.

The use of the centering and guiding device of the second embodiment of the invention will be understood better with the aid of the following description.

To produce a hole in the jaw of a patient, the practitioner mounts the centering and guiding device represented in FIGS. 5 and 6 on the dental handpiece 6, engaging the longitudinal support rod 19 in the receiving sleeve 20 (FIG. 9). The practitioner then fits the first drill bit 5 to be used to start producing a hole.

Once the drill bit 5 has been fitted, the practitioner adjusts the support means 3 by means of the rack on the longitudinal support rod 19 and the locking means 21 to adjust the axial position of the guide sleeve 4 relative to the drill bit with the guide sleeve 4 in the low position (FIG. 5).

The spring means 15 allow a known particular axial movement of the guide sleeve 4 between its low position and its high position. Accordingly, by accurately adjusting the low position of the guide sleeve 4, and knowing the axial movement value of the guide sleeve 4 between its low position and its high position and the first height h1, the depth to which the drill bit 5 will drill is known accurately.

In practice, the spring means 15 and the support means 3 are chosen so that the guide sleeve 4 is movable on the support means 3 with an axial stroke of at least approximately 15 mm between the low position and the high position. Thus the centering and guiding device of the invention can be used to install implants entering up to at least 15 mm into the jawbone of the patient, which is the most widely used market standard.

When the axial position of the guide sleeve 4 has been adjusted, the practitioner engages the drill bit 5 and the guide sleeve 4 in the tubular drilling bush 2 by a movement in the axial direction III-III (FIG. 8) illustrated by the arrow 22.

During this movement, the abutment plate 16*a* comes to bear against the open upper end 2*b* of the tubular drilling bush 2 (FIG. 9). The practitioner then continues to drill the jaw of the patient, compressing the spring means 15 and executing the whole of the authorized axial displacement of at least 15 mm. At the end of this axial displacement, the guide sleeve 4 is in the high position and the depth of the hole had been reached: the practitioner can then withdraw the drill bit 5 and the guide sleeve 4 from the tubular drilling bush 2 and continue drilling with another drill bit 5 of greater diameter.

Example 2

Adjustment of the Device of the Second Embodiment to Drill a Hole 8 Mm Deep in the Jaw of the Patient In this example, the first height h1 is 9 mm, the axial movement allowed by the spring means 15 is 15 mm and the axial length L5 of the guide sleeve 4 is 8 mm.

To adjust conveniently the axial position of the guide sleeve 4, the practitioner mounts the drill bit 5 and the centering and guiding device of the second embodiment of the invention on the dental handpiece 6.

The rack of the support rod 19 is immobilized in the receiving sleeve 20 so that, when the spring means 15 are compressed (guide sleeve 4 in high position), the proximal end 4*a* of the guide sleeve is at a distance from the distal end 5*b* of the drill bit 5 equal to the sum of the first height h1 and the required depth of the hole (8 mm in this example), that is to say 17 mm here. In the low position, the proximal end 4*a* of the guide sleeve 4 is therefore offset from the distal end 5*b* of the drill bit 5 by 2 mm in the direction of the proximal end 5*a* of the drill bit 5. In the low position, the distal end 5*b* of the drill bit 5 is therefore inside the guide sleeve 4.

Example 3

Adjustment of the Device of the Second Embodiment to Drill a Hole 15 Mm Deep in the Jaw of the Patient In this example, the first height h1 is 9 mm, the axial movement allowed by the spring means 15 is 15 mm and the axial length L5 of the guide sleeve 4 is 8 mm.

In order to adjust conveniently the axial position of the guide sleeve 4, the practitioner mounts the drill bit 5 and the centering and guiding device of the second embodiment of the invention on the dental handpiece 6. The rack of the support rod 19 is immobilized in the receiving sleeve 20 so that, when the spring means 15 are compressed (guide sleeve 4 in high position), the proximal end 4*a* of the guide sleeve is at a distance from the distal end 5*b* of the drill bit 5 equal to the sum of the first height h1 and the required depth of the hole (15 mm in this example), i.e. 24 mm here.

In the low position, the proximal end 4*a* of the guide sleeve 4 is therefore offset from the distal end 5*b* of the drill bit 5 by 9 mm in the direction of the proximal end 5*a* of the drill bit 5. In the low position, the distal end 5*b* of the drill bit 5 therefore extends 1 mm beyond the distal end 4*b* of the guide sleeve 4.

It is seen that, in each of the above examples 2 and 3, the guide sleeve 4, the length of which is 8 mm, is always engaged at least 4 mm in the tubular drilling bush 2 even before the drill bit 5 begins to drill the jawbone of the patient. This guarantees effective guiding of the drill bit 5 even before drilling begins, the guide sleeve 4 being engaged in the tubular drilling bush 2 to a distance more or less substantially equal to or greater than its outside diameter d2 (which is 4.17 mm or 5.17 mm according to the most widely available market standards). This remains the case for identical adjustments and a guide sleeve 4 with a length L5 of 4 mm.

The present invention is not limited to the embodiments explicitly described but includes variants and generalizations thereof within the scope of the following claims.

The invention claimed is:

1. Centering and guiding device, comprising:
   at least one drill bit (5) having a proximal end (5a) and a free distal end (5b) with a proximal section (50a) for connection to the dental handpiece (6) and a distal cutting section (50b),
   a tubular guide sleeve (4) adapted to be engaged with a small clearance in a tubular drilling bush (2) of a surgical guide (1) used while drilling a hole for an implant (29) in the jaw (30) of a patient,
   support means (3) holding the tubular guide sleeve (4) permanently coaxial with and slidable relative to said at least one drill bit (5), and adapted to cause engagement of the tubular guide sleeve (4) in the tubular drilling bush (2) at the latest as soon as said at least one drill bit (5) begins to drill the jaw (30) of the patient,
   wherein the support means (3) include a smooth cylindrical intermediate section (5c) of said at least one drill bit (5) with an outside diameter (d3) substantially equal to or slightly less than an inside diameter (d4) of the tubular guide sleeve (4) and on which the tubular guide sleeve (4) is slidably engaged,
   and wherein the tubular guide sleeve (4) includes friction means (9) to slide frictionally, exclusively on said smooth cylindrical intermediate section (5c), in a direction of the proximal end (5a) of said at least one drill bit (5),
   and wherein the friction means comprises means for producing a reaction force that opposes an axial force applied by a practitioner during penetration of the drill bit into the jaw of the patient.

2. Device according to claim 1, including a plurality of drill bits (5) with distal cutting sections (50b) of different diameters (d7) and all including a smooth cylindrical intermediate section (5c) of the same outside diameter (d3) substantially equal to or slightly less than the inside diameter (d4) of the tubular guide sleeve (4).

3. Device according to claim 1, wherein the smooth cylindrical intermediate section (5c) extends over a first length (L3) from the distal cutting section (50b) greater than a total length (L6) of the tubular guide sleeve (4) by at least approximately 8 mm.

4. Device according to claim 1, wherein the tubular guide sleeve (4) includes penetration means (8) to facilitate its engagement in the tubular drilling bush (2), said penetration means (8) comprising a bevelled distal end (4b) on the tubular guide sleeve (4).

5. Device according to claim 1, wherein the friction means (9) include an O-ring (10) having an inside diameter (d5) slightly less than or substantially equal to the outside diameter (d3) of the smooth cylindrical intermediate section (5c) and housed in an interior annular groove (11) of the tubular guide sleeve (4).

6. Device according to claim 1, further including adjustable means for limiting the depth of penetration of the drill bit (5) in the jaw (30) of the patient.

7. Device according to claim 6, said adjustable means including abutment means (13) adapted to be fastened to the dental handpiece (6) and adapted to come to bear on the proximal end (4a) of the tubular guide sleeve (4) or on an open upper end (2b) of the tubular drilling bush (2) at the end of penetration of the drill bit (5) into the jaw (30) of the patient.

8. Device according to claim 1, further including spring return means (24) continuously urging the tubular guide sleeve (4) toward the free distal end (5b) of the drill bit (5).

9. Set comprising a centering and guiding device according to claim 1, further comprising a surgical guide (1), wherein:
   when in position on the jaw (30) of the patient, the surgical guide (1) holds an open upper end (2b) of the tubular drilling bush (2) at a particular first height (h1) above a distal end (29a) of an implant (29) which is screwed into the jaw (30) of the patient,
   the distal cutting section (50b) has an axial length (L1) less than the first height (h1), and
   the distal cutting section (50b) has an outside diameter (d7) greater than the outside diameter (d3) of the smooth intermediate section (5c).

10. Set according to claim 9, wherein:
    when in position on the jaw (30) of the patient, the surgical guide (1) holds the open upper end (2b) of the tubular drilling bush (2) at a particular first height (h1) above the distal end (29a) of the implant (29) at the end of screwing it into the jaw (30) of the patient,
    the tubular guide sleeve (4) has a proximal end (4a) with an outside diameter (d6) greater than the inside diameter (d1) of the tubular drilling bush (2) and with a shoulder (12) with an abutment face (12a) oriented in the direction of its distal end (4b) and intended to come to bear against the open upper end (2b) of the tubular drilling bush (2) at the end of penetration of the tubular guide sleeve (4) into the tubular drilling bush (2), and
    the abutment face (12a) of the shoulder (12) of the tubular guide sleeve (4) is at a distance (L2) less than the first height (h1) from the distal end (4b) of the tubular guide sleeve (4).

11. Set according to claim 10, wherein the abutment face (12a) of the shoulder (12) of the tubular guide sleeve (4) is at a distance (L2) between approximately 4 mm and approximately 8 mm from the distal end (4b) of the tubular guide sleeve (4).

12. Device according to claim 1, wherein the dimensions of the support means (3) are such as to cause engagement of the tubular guide sleeve (4) in the tubular drilling bush (2) to a length substantially at least equal to the inside diameter (d1) of the tubular drilling bush (2) at the latest before said at least one drill bit (5) begins to drill the jaw (30) of the patient.

13. Centering and guiding device, comprising:
    a tubular guide sleeve (4) adapted to be engaged with a small clearance in a tubular drilling bush (2) of a surgical guide (1) used while drilling a hole for an implant (29) in the jaw (30) of a patient,
    support means (3) adapted to hold the tubular guide sleeve (4) permanently coaxial with and slidable relative to at least one drill bit (5), and adapted to cause engagement of the tubular guide sleeve (4) in the tubular drilling bush (2) at the latest as soon as said at least one drill bit (5) begins to drill the jaw (30) of the patient,
    wherein:
    the tubular guide sleeve (4) is movable on the support means (3) between a low position and a high position, the support means (3) are adapted to be fastened to the dental handpiece (6) and include adjustment means for adjusting the axial position of the tubular guide sleeve (4) relative to the drill bit (5) when the tubular guide sleeve (4) is in the low position, and in the high position, first abutment means (14) prevent the tubular guide sleeve (4) from being moved further beyond the high position in the direction of the proximal end of the drill bit, the first abutment means (14) are held by the support means (3), further including a surgical guide (1), wherein:

the surgical guide (1) holds an open upper end (2b) of the tubular drilling bush (2) at a particular first height (h1) above the distal end (29a) of the implant (29) at the end of screwing it into the jaw (30) of the patient, the tubular guide sleeve (4) has an axial length (L5) less than the first height (h1), and the proximal end (4a) of the tubular guide sleeve (4) is fastened to second abutment means (16) adapted to come to bear against the open upper end (2b) of the tubular drilling bush (2) at the end of penetration of the tubular guide sleeve (4) into the tubular drilling bush (2), and wherein:

the second abutment means (16) include an abutment plate (16a) extending radially away from the longitudinal axis (II-II) of the tubular guide sleeve (4), the first abutment means (14) include a support plate (17) parallel to the abutment plate (16a) and situated in a plane offset longitudinally relative to the abutment plate (16a), the support means (3) include two parallel guide columns (18a, 18b) providing a sliding connection between the support plate (17) and the abutment plate (16a), spring means (15) include two coil springs (19a, 19b) interleaved between the abutment plate and the support plate (17) and urging the support plate (17) and abutment plate (16a) away from each other, and the support means (3) include a longitudinal support rod (19) fastened to the support plate (17) and adapted to be fixed to the dental handpiece (6).

14. Device according to claim 13, wherein spring means (15) carried by the support means (3) continuously return the tubular guide sleeve (4) toward its low position.

15. Device according to claim 13, wherein the tubular guide sleeve (4) includes penetration means (8) to facilitate its engagement in the tubular drilling bush (2), said penetration means (8) comprising a bevelled distal end (4b) on the tubular guide sleeve (4).

16. Device according to claim 13, wherein the tubular guide sleeve (4) is movable on the support means (3) over an axial stroke of at least approximately 15 mm between the low position and the high position.

17. Device according to claim 13, wherein:

the longitudinal support rod (19) is formed with a rack, the dental handpiece (6) includes a longitudinal sleeve (20) for receiving the longitudinal support rod (19) and locking means (21) cooperating with the rack of the longitudinal support rod (19), the longitudinal receiving sleeve (20) includes an internal bore with a cross section of complementary shape to the cross section of the longitudinal support rod (19), and the cross sections of the longitudinal support rod (19) and the internal bore of the longitudinal receiving sleeve (20) prevent relative rotation between them.

18. Device according to claim 13, wherein the dimensions of the support means (3) are such as to cause engagement of the tubular guide sleeve (4) in the tubular drilling bush (2) to a length substantially at least equal to the inside diameter (d1) of the tubular drilling bush (2) at the latest before said at least one drill bit (5) begins to drill the jaw (30) of the patient.

* * * * *